(12) United States Patent
Danielmeier et al.

(10) Patent No.: US 7,759,452 B2
(45) Date of Patent: Jul. 20, 2010

(54) ASPARTIC ESTER FUNCTIONAL COMPOUNDS

(75) Inventors: Karsten Danielmeier, Solingen-Burg (DE); Douglas A. Wicks, Hattiesburg, MS (US); Karen Marie Henderson, Coraopolis, PA (US); Evan Randall Minnich, Pittsburgh, PA (US); John J. McLafferty, Hicksville, NY (US); Stephanie A. Strazisar, Venetia, PA (US); Kurt C. Frisch, Jr., Upper St. Clair, PA (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 0 days.

(21) Appl. No.: 12/354,036

(22) Filed: Jan. 15, 2009

(65) Prior Publication Data

US 2009/0142601 A1 Jun. 4, 2009

Related U.S. Application Data

(62) Division of application No. 10/890,873, filed on Jul. 14, 2004, now abandoned.

(51) Int. Cl.
*C08G 18/34* (2006.01)
*C08G 18/42* (2006.01)
*C08G 69/10* (2006.01)
*C07C 229/00* (2006.01)
*C07C 229/34* (2006.01)

(52) U.S. Cl. ............... 528/328; 528/272; 528/84; 528/256; 427/256; 427/207.1; 560/15; 560/44; 156/330.9

(58) Field of Classification Search ............... 528/328, 528/272, 84, 256; 427/256, 270.1; 560/15, 560/44; 156/330.9
See application file for complete search history.

(56) References Cited

U.S. PATENT DOCUMENTS

| | | | |
|---|---|---|---|
| 2,596,200 | A | 5/1952 | Bestian et at |
| 2,677,681 | A | 5/1954 | Gill |
| 3,124,605 | A | 3/1964 | Wagner |
| 3,183,112 | A | 5/1965 | Gemassmer |
| 3,358,010 | A | 12/1967 | Britain |
| 3,501,557 | A | 3/1970 | Brois |
| 3,644,490 | A | 2/1972 | Schmelzer et at |
| 3,769,318 | A | 10/1973 | Windemuth et at |
| 3,862,973 | A | 1/1975 | Dietrich et at |
| 3,903,126 | A | 9/1975 | Woerner et at |
| 3,903,127 | A | 9/1975 | Wagner et al |
| 4,051,165 | A | 9/1977 | Wagner et al. |
| 4,147,714 | A | 4/1979 | Hetzel et al. |
| 4,160,080 | A | 7/1979 | Koenig et al. |
| 4,177,342 | A | 12/1979 | Bock et al. |
| 4,220,749 | A | 9/1980 | Reichmann et al. |
| 5,124,427 | A | 6/1992 | Potter et al. |
| 5,126,170 | A | 6/1992 | Zweiner et al. |
| 5,208,334 | A | 5/1993 | Potter et al. |
| 5,235,018 | A | 8/1993 | Potter et al. |
| 5,412,056 | A | 5/1995 | Zweiner et al. |
| 5,516,873 | A | 5/1996 | Hicks et al. |
| 5,623,045 | A | 4/1997 | Zweiner et al. |
| 5,736,604 | A | 4/1998 | Luthra |
| 5,821,326 | A | 10/1998 | Kurek et al. |
| 5,914,383 | A | 6/1999 | Richter et al. |
| 6,384,175 | B1 | 5/2002 | Danielmeier et al. |

FOREIGN PATENT DOCUMENTS

| | | |
|---|---|---|
| EP | 0573860 A1 | 12/1993 |
| EP | 667362 A1 | 8/1995 |
| WO | 0020481 A1 | 4/2000 |
| WO | 0020482 A1 | 4/2000 |

OTHER PUBLICATIONS

Organic Coatings Science and Technology (month Unavailable) 1992, Chapter 8, pp. 120-132, Z. Wicks, Jr., et al, "Polyester Reins".
Pihko P M et al: "Enantiospecific synthesis of isomers of AES, a new enviromentally friendly chelating agent" Tetrahedron, Elsevier Science Publishers, Amsterdam, NL, vol. 60, No. 48, Nov. 22, 2004, pp. 10949-10954, XP004608836 ISSN: 0040-4020 Scheme 4, compounds 12, 15.
Database Beilstein [Online] Beilstein Institute for Organic Chemistry, Frankfurt-Main, DE; XP002374681 retrieved from MDL Database accession No. BRN 3651091; BRN 3634895 *abstract* & Dutta et al.: J. Pharm, Sci., vol. 79, No. 5, 1990, pp. 447-452.
Database Beilstein [Online] Beilstein Institute for Organic Chemistry, Frankfurt-Main, DE; XP002374682 retrieved from MDL Dtabase accession No. BRN 361230 *abstract* & Cardellini et al.: Ann. Chim., vol. 58, 1968, p. 914, Rome.

(Continued)

*Primary Examiner*—Duc Truong
(74) *Attorney, Agent, or Firm*—Robert S. Klemz; Noland J. Cheung

(57) ABSTRACT

A functional aspartate prepared by A) reacting an aziridine with a Michael-acceptor molecule to form an aziridinyl aspartate, and B) reacting the aziridinyl aspartate with an active hydrogen containing compound to form the functional aspartate. The functional aspartate can be used in adhesive, sealant or coating compositions that also include an isocyanate functional material. The composition can be used in a method of bonding a first substrate to a second substrate that includes applying a coating of the above-identified adhesive composition to at least one surface of the first substrate or the second substrate, and contacting a surface of the first substrate with a surface of the second substrate, where at least on of the contacting surfaces has the coating applied thereto. The composition can also be used to coat substrates.

19 Claims, No Drawings

OTHER PUBLICATIONS

Database Beilstein [Online] Beilstein Institute for Organic Chemistry, Frankfurt-Main, DE; XP002374683 retrieved from MDL Database accession No. BRN 4589202 *abstract* & Voronkov et al.: Khim, Geterotsikl. Soedin., vol. 24, No. 11, 1988, pp. 1563-1565.

Database Beilstein [Online] Beilstein Institute for Organic Chemistry, Frankfurt-Main, DE; XP02374684 retrieved from MDL BRN 4601394 *abstract* BRN 4560987 & Voronkov et al.; Khim. Geterotsikl. Soedin., vol. 20, No. 10, 1984, pp. 1340-1342.

Database Beilstein, Databse Access. No. BRN 4561323 & Voronkov et al, Khim Geterotsikl. Soedin., vol. 20, No. 10, (month unavailable) 1984, pp. 1340-1342.

ASPARTIC ESTER FUNCTIONAL COMPOUNDS

CROSS REFERENCE TO RELATED APPLICATIONS

This application is a divisional application of Ser. No. 10/890,873, filed on Jul. 14, 2004 (now abandoned).

FIELD OF THE INVENTION

The present invention relates to functional aspartic ester compounds and their use in adhesive, sealant, and coating compositions.

BACKGROUND ART

Aspartic esters represent a unique class of reactants in adhesive, coating, and sealant formulations. Their reactivity typically lies between slow classical polyols and faster reacting primary and secondary amines.

U.S. Pat. Nos. 5,412,056, 5,623,045, 5,126,170, and 5,821,326 disclose coating compositions in which the binding agent is a two-component system containing a polyisocyanate component and an isocyanate-reactive component. The latter component includes at least one aspartic acid diester group formed by reacting an amine with a maleic or fumaric diester.

EP 0 667 362 A1 discloses coating compositions including a polyisocyanate component, a component that includes at least one aspartic acid diester group formed by reacting an amine with a maleic or fumaric diester, and a water-adsorbing zeolite.

Adhesives are commonly used to join or fasten two or more adherends. Adherends are considered as being any two or more materials, or pieces of material that are being joined together, including wood, metals, plastics, paper, ceramics, stone, glass, concrete, etc. Adhesives used for these purposes are based on a wide range of technologies, including elastomer/solvent/resin mixtures, epoxies, latexes, polyurethanes, silicones, cyanoacrylates, acrylics, hot melts, and others. Such adhesives can have one or more drawback, such as they may contain solvents which are toxic and often flammable, they can be incompatible with one or more classes of adherends, they can have undesirably long cure times and in many cases the bonds they form of are of insufficient strength.

It is often desirable for coatings applied to substrates to provide a desirable appearance, in many cases by applying multiple coating layers, the last of which can be a pigmented or unpigmented topcoat. Unfortunately, as the article containing the coated substrate ages, scratches that occur through normal "wear and tear", tend to deteriorate the appearance of the coated surface of the substrate, A sealant is typically a thin film, often containing a plastic, that is applied onto one or more surfaces on one or more substrates to prevent passage of a liquid or gas through the film. The sealant can be used to prevent exposure of the substrate or is often additionally used to prevent exposure via defects in a substrate or between gaps that can exist between substrates.

Oftentimes, high molecular weight compounds containing aspartic esters are desired for various adhesive, coating and sealant applications. However, the corresponding precursors often react very slowly leading to undesirably long processing times, poor conversion to the desired product, and/or impure products.

Additionally, desired functionality and/or molecular architectures in the aspartic ester materials may not be achievable using the established amine-maleic/fumaric ester synthetic pathway. This limits the possible aspartic ester containing materials available for formulation.

U.S. Pat. No. 2,569,200 discloses polyvalent alkylene imine esters and methods for preparing them.

There is an established need in the art for alternative synthetic pathways that can provide a wider range of molecular architectures and functional groups for aspartic ester containing compounds that can be made efficiently.

SUMMARY OF THE INVENTION

The present invention is directed to functional dialkyl aspartic esters (aspartates) according to the formula:

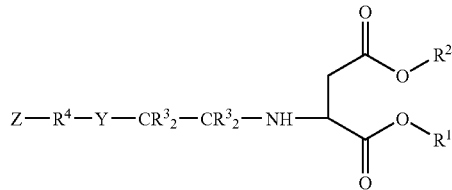

where
$R^1$ and $R^2$ are independently $C_1$-$C_8$ linear, branched or cyclic alkyl,
each occurrence of $R^3$ is independently selected from H, $C_1$-$C_{20}$ linear, branched, or cyclic alkyl, aryl, alkaryl or aralkyl,
Y is a linking group selected from the group consisting of —O—, —S—, —NR$^5$—,
—O—P(O)$_2$—O—, —P(O)$_2$—O—, —S(O)$_2$—O—,

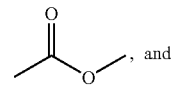, and a group resulting from the removal of an acidic hydrogen from a carbon that is positioned adjacent to one or more electron withdrawing groups according to one of the formulas

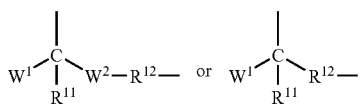

where
$R^5$ is H or $C_1$-$C_3$ linear or branched alkyl,
$W^1$ is an electron withdrawing group selected from the group consisting of nitrile, $R^{11}$—CO—, nitro, carboxylic acids and their corresponding salts, $C_1$-$C_{24}$ linear, branched or cyclic alkyl, alkenyl, aryl, alkaryl, or aralkyl esters of carboxylic acids, and $C_1$-$C_{24}$ linear, branched or cyclic alkyl sulfonyl,
$W^2$ is a ketone,
$R^{11}$ is selected from H. —OH, $C_1$-$C_{24}$ linear, branched or cyclic alkyl, aryl, alkaryl, or aralkyl, which may contain one or more hetero atoms selected from O, S, and/or N,
$R^{12}$ is $C_1$-$C_{24}$ linear, branched or cyclic alkylene, arylene, alkarylene, or aralkylene, which may contain one or more hetero atoms selected from O, S, and/or N, and $R^4$ is a linking group selected from the group consisting of $C_1$-$C_{24}$ linear, branched or cyclic alkylene, arylene, alkarylene, or aralkylene, —(—[$CHR^7$-]$_n$—O—)p-$R^8$—, where $R^7$ is $C_1$-$C_3$ linear or branched alkyl or aklylol, n is 1 to 4, and p is 1 to 1,000,

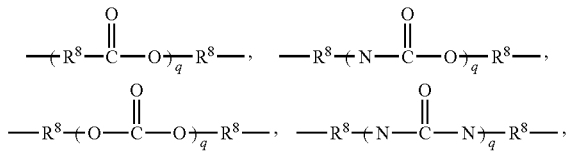

where q is 1 to 1,000, and each occurrence of $R^8$ is independently selected from $C_1$-$C_{24}$ linear, branched or cyclic alkylene, alkenylene, arylene, alkarylene, or aralkylene, optionally including substituent hydroxyl, carboxylic acid, or $C_1$-$C_8$ linear, branched or cyclic carboxylic acid ester groups,

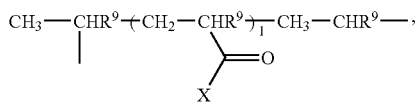

where r is 1 to 10,000, $R^9$ is $C_1$-$C_3$ linear or branched alkyl,

X is —$OR^{10}$ or —$NR^5_2$, where $R^5$ is as defined above, $R^{10}$ is H or $C_1$-$C_{24}$ linear, branched or cyclic alkyl, aryl, alkaryl, and aralkyl, and combinations thereof, and Z is selected from —H, —$OR^{10}$, $R^4$—$OR^{10}$, —$NR^5_2$, —$R^4$—$NR^5_2$, —SH, —$R^4$—SH,

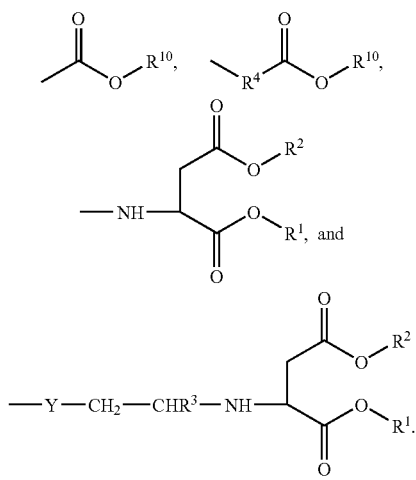

The present invention is also directed to a method of preparing a functional aspartate and the functional aspartate resulting from the method. The method includes A) reacting an aziridine with a Michael-acceptor molecule to form an aziridinyl aspartate, and B) reacting the aziridinyl aspartate with an active hydrogen containing compound to form the functional aspartate.

The present invention is further directed to adhesive, sealant or coating compositions that include i) the above described functional aspartates, and ii) an isocyanate functional material.

DETAILED DESCRIPTION OF THE INVENTION

Other than in the operating examples, or where otherwise indicated, all numbers or expressions referring to quantities of ingredients, reaction conditions, etc., used in the specification and claims are to be understood as modified in all instances by the term "about." Various numerical ranges are disclosed in this patent application. Because these ranges are continuous, they include every value between the minimum and maximum values. Unless expressly indicated otherwise, the various numerical ranges specified in this application are approximations.

As used herein the term "alkyl" refers to a monovalent radical of an aliphatic hydrocarbon chain of general formula $C_sH_{2s+1}$, where s is the number of carbon atoms, or ranges therefore, as specified. The term "substituted alkyl" refers to an alkyl group, where one or more hydrogens are replaced with a non-carbon atom or group, non-limiting examples of such atoms or groups include halides, amines, alcohols, oxygen (such as ketone or aldehyde groups), and thiols.

As used herein the terms "cyclic alkyl" or "cycloalkyl" refer to a monovalent radical of an aliphatic hydrocarbon chain that forms a ring of general formula $C_sH_{2s-1}$, where s is the number of carbon atoms, or ranges therefore, as specified. The term "substituted cycloalkyl" refers to a cycloalkyl group, containing one or more hetero atoms, non-limiting examples being —O—, —NR—, and —S— in the ring structure, and/or where one or more hydrogens are replaced with a non-carbon atom or group, non-limiting examples of such atoms or groups include halides, amines, alcohols, oxygen (such as ketone or aldehyde groups), and thiols. R represents an alkyl group of from 1 to 24 carbon atoms.

As used herein, the term "aryl" refers to a monovalent radical of an aromatic hydrocarbon. Aromatic hydrocarbons include those carbon based cyclic compounds containing conjugated double bonds where 4t+2 electrons are included in the resulting cyclic conjugated pi-orbital system, where t is an integer of at least 1. As used herein, aryl groups can include single aromatic ring structures, one or more fused aromatic ring structures, covalently connected aromatic ring structures, any or all of which can include heteroatoms. Non-limiting examples of such heteroatoms that can be included in aromatic ring structures include O, N, and S.

As used herein, the term "alkylene" refers to acyclic or cyclic divalent hydrocarbons having a carbon chain length of from $C_1$ (in the case of acyclic) or $C_4$ (in the case of cyclic) to $C_{25}$, typically $C_2$ to $C_{12}$, which may be substituted or unsubstituted, and which may include substituents. As a non-limiting example, the alkylene groups can be lower alkyl radicals having from 1 to 12 carbon atoms. As a non-limiting illustration, "propylene" is are intended to include both n-propylene and isopropylene groups; and, likewise, "butylene" is intended to include both n-butylene, isobutylene, and t-butylene groups.

As used herein, the term "(meth)acrylic" and "(meth)acrylate" are meant to include the corresponding derivatives of acrylic acid and methacrylic acid, without limitation.

As used herein, the term "cure" (or "curing") is intended to include both crosslinking of the adhesive, sealant, or coating composition components and film formation as a result of evaporation of water and, if present, other solvents and diluents along with the development of physical and chemical properties in the resultant film such as bond strength and peel strength.

As used herein, the term "crosslink" or "crosslinking" refers to the formation of short chains of molecules linking two longer molecular chains together through the reaction of two or more functional groups on the short chains.

The present invention is directed to a method of making functional dialkyl aspartic acid esters ("aspartate" or "aspartates") and aspartates that can be made using the method. Embodiments of the invention include a method that includes:

A) reacting an aziridine with a Michael-acceptor molecule to form an aziridinyl aspartate, and B) reacting the aziridinyl aspartate with an active hydrogen containing compound to form the functional aspartate.

As used in the present invention, the term "aziridine" refers to compounds according to Formula I,

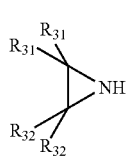

(I)

where each occurrence of $R^{31}$ and $R^{32}$ are independently selected from H, $C_1$-$C_{20}$ linear, branched, or cyclic alkyl, aryl, alkaryl or aralkyl, in some cases H and $C_1$-$C_3$ linear or branched alkyl, and in other cases H or $C_1$-$C_2$ linear or branched alkyl groups. In an embodiment of the invention, $R^{32}$ is H and at least one occurrence of $R^{31}$ is H. In another embodiment of the invention, the aziridine is selected from unsubstituted aziridine (ethylene imine), 2-methyl aziridine, 2-ethyl aziridine, 2-n-propyl aziridine, and 2-isopropyl aziridine.

As used in the present invention, the term "Michael-acceptor molecule" refers to a molecule that contains one or more electron withdrawing groups (EWG) that cause a carbon in a carbon-carbon double bond to be electro positive and a good place for nucleophilic attack. Any suitable Michael-acceptor molecule, molecules or polymers containing a Michael-acceptor in the backbone can be used in the present invention. A non-limiting example of a polymer backbone Michael-acceptor group is the maleic ester group in the formula below:

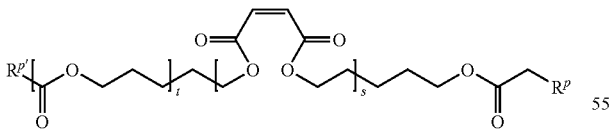

where $R^p$ and $R^{p'}$ are independently $C_1$-$C_{20}$ linear, branched or cyclic alkyl, aryl, alkaryl or aralkyl, and s and t are independently 1 to 1,000, in some cases 1 to 500, and in other cases 1 to 100.

In an embodiment of the invention, the suitable Michael-acceptor molecules include, but are not limited to those containing a carbon-carbon double bond and one or more EWGs selected from ketones, nitriles, nitro groups, carboxylic acids and their corresponding salts, $C_1$-$C_{24}$ linear, branched or cyclic alkyl, alkenyl, aryl, alkaryl, or aralkyl esters of carboxylic acids, and $C_1$-$C_{24}$ linear, branched or cyclic alkyl sulfonyl groups.

In a particular embodiment of the invention, the suitable Michael-acceptor molecules include, but are not limited to $C_1$-$C_8$ linear, branched or cyclic dialkyl esters of maleic acid, $C_1$-$C_8$ linear, branched or cyclic dialkyl esters of fumaric acid, maleimide, $C_1$-$C_8$ linear, branched or cyclic N-alkyl maleimide, mono-amides of maleic acid, mono-amides of fumaric acid, di-amides of maleic acid, di-amides of fumaric acid, $C_1$-$C_8$ linear, branched or cyclic N-alkyl amides of maleic acid, and $C_1$-$C_8$ linear, branched or cyclic N-alkyl amides of fumaric acid.

As used herein, the term "active hydrogen containing compound" refers to compounds that that contain a hydrogen atom that is sufficiently acidic to allow the compound to effectuate a ring opening reaction of the aziridine moiety.

In an embodiment of the invention, the active hydrogen containing compounds include, but are not limited to $C_1$-$C_{24}$ linear, branched or cyclic alkylenes, alkenylenes, arylenes, alkarylenes, or aralkylenes, polyethers, polyesters, or poly(meth)acrylic molecules containing two or more functional groups selected from the group consisting of hydroxyl, carboxylic acid, thiol, amine, acidic CH groups, and combinations thereof.

As used herein the terms "(meth)acrylic" and "(meth)acrylate" encompass compounds that include moieties of or derived from both methacrylic acid and its corresponding esters, amides, and salts as well as acrylic acid and its corresponding esters, amides, and salts.

In an embodiment of the invention, the active hydrogen containing compounds include at least one and in some cases a number average of at least 1.5, in other cases at least 2 active hydrogen containing groups.

In an embodiment of the invention, the active hydrogen containing compound can have the following Formula II:

$$Z—R^4—Y'$$ (II)

where Y' can be a group selected from —OH, —SH, —$NR^5H$, —COOH, —O—$P(O)_2$—OH,

—$P(O)_2$—OH, —$S(O)_2$—OH, and a group containing an acidic hydrogen on a carbon positioned adjacent to one or more electron withdrawing groups according to one of Formulas III and/or Formula IV:

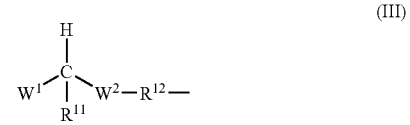

(III)

(IV)

where $R^5$ can be H or $C_1$-$C_3$ linear or branched alkyl, $W^1$ can be an electron withdrawing group selected from nitrile, $R^{11}$—CO—, nitro, carboxylic acids and their corresponding salts, $C_1$-$C_{24}$ linear, branched or cyclic alkyl, alkenyl, aryl, alkaryl, or aralkyl esters of carboxylic acids, and $C_1$-$C_{24}$ linear, branched or cyclic alkyl sulfonyl, $W^2$ can be a ketone, $R^{11}$ can be selected from H, OH, $C_1$-$C_{24}$ linear, branched or cyclic alkyl, aryl, alkaryl, or aralkyl, which may contain one or more hetero atoms selected from O, S, and/or N, and $R^{12}$ can be $C_1$-$C_{24}$ linear, branched or cyclic alkylene, arylene, alkarylene, or aralkylene, which may contain one or more hetero atoms selected from O, S, and/or N.

In Formula II, $R^4$ can be a linking group selected from a $C_1$-$C_{24}$ linear, branched or cyclic alkylene, arylene, alkarylene, or aralkylene group, —(—[CHR$^7$—]$_n$—O—)$_p$—R$^8$—, where $R^7$ can be $C_1$-$C_3$ linear or branched alkyl or aklylol, n can be 1 to 4, in some cases 2 or 3, and p can be 1 to 1,000, in some cases 1 to 500, in other cases 2 to 250, in some situations 2 to 100 and in other situations 2 to 50,

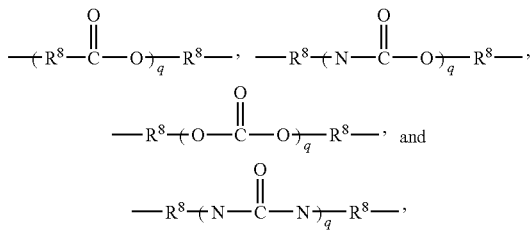

where q is 1 to 1,000, in some cases 1 to 500, in other cases 2 to 250, in some situations 2 to 100 and in other situations 2 to 50, and each occurrence of $R^8$ is independently selected from $C_1$-$C_{24}$ linear, branched or cyclic alkylene, alkenylene, arylene, alkarylene, or aralkylene, optionally including substituent hydroxyl, carboxylic acid, or $C_1$-$C_8$ linear, branched or cyclic carboxylic acid ester groups,

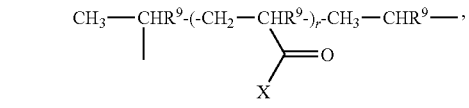

where r is 1 to 10,000, in some cases 1 to 500, in other cases 2 to 250, in some situations 2 to 100 and in other situations 2 to 50, $R^9$ is $C_1$-$C_3$ linear or branched alkyl, X is —OR$^{10}$ or —NR$^5_2$, where $R^5$ is as defined above, $R^{10}$ is H or $C_1$-$C_{24}$ linear, branched or cyclic alkyl, aryl, alkaryl, and aralkyl, and combinations thereof.

Also in Formula II,

Z can be selected from —H, —OR$^{10}$, —R$^4$—OR$^{10}$, —NR$^5_2$, —R$^4$—NR$^5_2$, —SH, —R$^4$—SH,

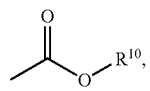 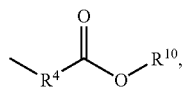

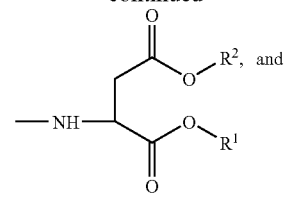

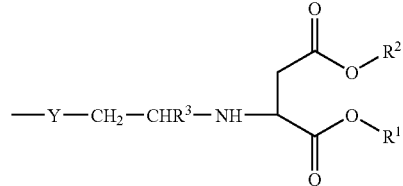

where $R^4$, $R^5$, and $R^{10}$ can be as described above and $R^1$ and $R^2$ are independently $C_1$-$C_8$, in some cases $C_2$-$C_6$ linear, branched or cyclic alkyl groups or a portion of a polymer backbone.

Particular embodiments of the invention are directed to functional aspartates where the group Z—R$^4$—Y' is a polyester radical. Some aspects of this embodiment are directed to situations where the polyester is a carboxylic acid functional polyester.

In another particular embodiments of the invention, the group Z—R$^4$—Y' in the active hydrogen containing compound of Formula II is a polyether radical in the functional aspartate. In some aspects of this embodiment, the polyether is a hydroxyl functional polyether.

Additional particular embodiments of the invention are directed to Z—R$^4$—Y' active hydrogen containing compounds of Formula II where the group Z—R$^4$—Y' is a poly (meth)acrylate containing one or more active hydrogen group. In some aspects of this embodiment the poly(meth)acrylate is a carboxylic acid functional polyacrylate.

In further particular embodiments of the invention, the active hydrogen containing compounds of Formula II contains a group Z—R$^4$—Y', which is a $C_1$-$C_{24}$ linear, branched or cyclic alkyl, alkenyl, aryl, alkaryl, or aralkyl dicarboxylic acid. In some aspects of this embodiment, the dicarboxylic acid is selected from adipic acid, malonic acid, succinic acid, maleic acid, fumaric acid, pentanedioc acid, hexanedioic acid, heptanedioic acid, octanedioic acid, nonadioic acid, and mixtures thereof.

In a further particular embodiment, the Michael-acceptor molecule is a diester or diamide of maleic acid where each ester or amide group is independently a $C_1$-$C_8$, in some cases $C_2$-$C_6$ linear, branched or cyclic alkyl group, the aziridine conforms to Formula I, and the active hydrogen containing compound conforms to Formula II, where Y' is a carboxylic acid.

In an embodiment of the present invention, a catalyst can be used in the method of making functional dialkyl aspartates. Appropriate catalysts can be used in either A) or B).

In a particular embodiment of the invention, a catalyst is used in A) can be selected from metal salts of saturated or unsaturated carboxylic acids, alcoholates, including, but not limited to sodium methylate and aluminum ethylate, and alkaline amides, including, but not limited to sodium amide.

In a particular embodiment of the invention, a catalyst is used in B), which can be selected from Bronstead acids or Lewis acids. Non-limiting examples of Lewis acids that can be used as a catalyst include tris-(pentafluorophenyl)borane;

metal halides such as $CuCl_2 \cdot 2H_2O$ or $BiCl_3$; and triflates (trifluoromethanesulfonate, abbreviated TF) of suitable metals such as $Yb(OTF)_3$, $LiNTF_2$, $Sn(OTF)_2$ or $Cu(OTF)_2$. Non-limiting examples of Bronstead acids that can be used as a catalyst include hydrochloric acid, sulfuric acid, and perchloric acid. In some aspects of this embodiment, heterogeneous catalysts can be used and the catalyst can include silica gel and/or montmorillonite clay.

As a non-limiting embodiment of preparing functional aspartates according to the invention, the Michael-acceptor molecule and aziridine according to Formula I are mixed at a temperature of less than 30 C. and stirred for from 30 minutes to 24 hours. A vacuum is applied to remove unreacted aziridine and/or an electrophilic agent is used to react with and scavenge the aziridine. The reaction provides an aziridinyl aspartate which is combined with an acid functional polyether (active hydrogen containing compound) and stirred for four to 24 hours. Completion of the reaction can be confirmed by chromatography, gel permeation chromatography (GPC) being a non-limiting example of such.

Embodiments of the invention are directed to functional dialkyl aspartates that can be made according to the present method. Particular embodiments of the invention are directed to functional dialkyl aspartates described according to Formula V:

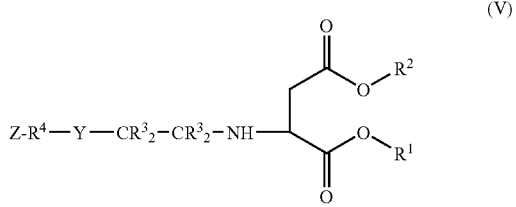

where $R^1$ and $R^2$ are independently $C_1$-$C_8$ linear, branched or cyclic alkyl, and each occurrence of $R^3$ is independently selected from H, $C_1$-$C_{20}$ linear, branched, or cyclic alkyl, aryl, alkaryl or aralkyl.

Also in Formula V, Y is a linking group that can be selected from —O—, —S—, —$NR^5$—, —O—$P(O)_2$—O—, $P(O)_2$—O—, —$S(O)_2$—O—,

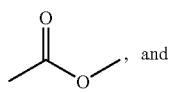 and a group resulting from the removal of the acidic hydrogen (H) from a carbon that is positioned adjacent to one or more electron withdrawing groups according to Formula III or Formula IV as shown in Formulas IIIa and IVa below, where $W^1$ and $W^2$ are as defined above.

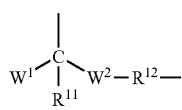

IIIa

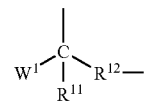

IVa

In Formula V, $R^4$ is a linking group as defined above and Z is a group as defined above.

Particular embodiments of the invention are directed to functional aspartates where the group Z—$R^4$—Y— is a polyester radical. Some aspects to this embodiment are directed to situations where the polyester is a carboxylic acid functional polyester.

In another particular embodiments of the invention, the group Z—$R^4$—Y— is a polyether radical in the functional aspartate. In some aspects of this embodiment, the polyether is a hydroxyl functional polyether.

Additional particular embodiments of the invention are directed to functional aspartates where the group Z—$R^4$—Y— is a poly(meth)acrylate radical. In some aspects of this embodiment the poly(meth)acrylate is a carboxylic acid functional polyacrylate.

In further particular embodiments of the invention, the functional aspartate contains a group Z—$R^4$—Y—, which is a monoester radical of a $C_1$-$C_{24}$ linear, branched or cyclic alkyl, alkenyl, aryl, alkaryl, or aralkyl dicarboxylic acid. In some aspects of this embodiment, the dicarboxylic acid is selected from adipic acid, malonic acid, succinic acid, maleic acid, fumaric acid, pentanedioc acid, hexanedioic acid, heptanedioic acid, octanedioic acid, nonadioic acid, and mixtures thereof.

In a particular embodiment of the invention, functional aspartate according to Formula V conforms to Formula Va:

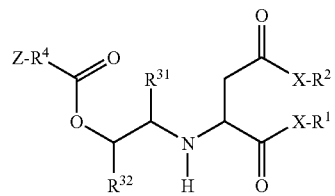

(Va)

where Z, $R^4$, $R^{32}$, $R^{31}$, $R^1$, and $R^2$ are as defined above and X can be O or $NR^5$ as defined above.

Embodiments of the present invention are directed to adhesive, sealant or coating compositions that include:
i) one or more of the functional dialkyl aspartates described above, and
ii) an isocyanate functional material.

In an embodiment of the invention, the isocyanate functional material can be a polyisocyanate containing from 2 to 6 isocyanate groups. In a particular embodiment, the polyisocyanate has a structure according to Formula VI:

$$OCN-R^{17}-NCO \qquad (VI)$$

where $R^{17}$ is selected from $C_2$ to $C_{24}$ linear, branched, and cyclic alkylene, arylene, and aralkylene, which may optionally contain one or more isocyanate groups.

In another particular embodiment of the invention, the polyisocyanate can be selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and 1,4-diisocyanate, 1-isocyanato-2-isocyanatomethyl cyclopentane, 1-isocyanato-3-isocyanatomethyl-3,5,5-trimethyl-cyclohexane, bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, $\alpha,\alpha,\alpha',\alpha'$-tetramethyl-1,3-diisocyanate, $\alpha,\alpha,\alpha',\alpha'$-1,4-xylylene diisocyanate, 1-isocyanato-1-methyl-4(3)-isocyanatomethyl cyclohexane, 2,4-hexahydrotoluylene diisocyanate, 2,6-hexahydrotoluylene diisocyanate, 1,3-phenylene diisocyanate, 1,4-phenylene diisocyanate, 2,4-toluylene diisocyanate, 2,6-toluylene diisocyanate, 2,4-diphenyl-methane diisocyanate, 4,4'-diphenyl-methane diisocyanate, 1,5-diisocyanato naphthalene and mixtures thereof.

In another embodiment of the invention, the polyisocyanates can include one or more polyisocyanate adducts containing biuret, urethane, uretdione, allophanate, isocyanurate, and/or iminooxadiazinedione groups.

Non-limiting examples of biuret group-containing polyisocyanates include those prepared according to the processes disclosed in U.S. Pat. Nos. 3,124,605; 3,358,010; 3,644,490; 3,862,973; 3,903,126; 3,903,127; 4,051,165; 4,147,714; or 4,220,749 the pertinent portions of which are herein incorporated by reference, by using co-reactants such as water, tertiary alcohols, primary and secondary monoamines, and primary and/or secondary diamines. These polyisocyanates can have an NCO content of 18 to 22% by weight and an average NCO functionality of from 3 to 3.5.

Non-limiting examples of urethane group-containing polyisocyanates include those prepared in accordance with the process disclosed in U.S. Pat. No. 3,183,112; the pertinent portions of which are herein incorporated by reference, by reacting excess quantities of polyisocyanates, in some cases diisocyanates, with low molecular weight glycols and polyols having molecular weights of less than 400, such as trimethylol propane, glycerine, 1,2-dihydroxy propane and mixtures thereof. The urethane group-containing polyisocyanates can have an NCO content of 12 to 20% by weight and an (average) NCO functionality of 2.5 to 3.

Non-limiting examples of uretdione diisocyanates include those prepared by oligomerizing a portion of the isocyanate groups of a diisocyanate in the presence of a suitable catalyst, e.g., a trialkyl phosphine catalyst, and which can be used in admixture with other aliphatic and/or cycloaliphatic polyisocyanates, particularly the isocyanurate group-containing polyisocyanates set forth above.

Non-limiting examples of allophanate group-containing polyisocyanates include those prepared according to the processes disclosed in U.S. Pat. Nos. 3,769,318; 4,160,080 and 4,177,342; the pertinent portions of which are herein incorporated by reference. The allophanate group-containing polyisocyanates can have an NCO content of from 12 to 21% by weight and an (average) NCO functionality of 2 to 4.5.

Non-limiting examples of isocyanurate and allophanate group-containing polyisocyanates include those prepared in accordance with the processes set forth in U.S. Pat. Nos. 5,124,427; 5,208,334 and 5,235,018; the pertinent portions of which are herein incorporated by reference. Such polyisocyanates can contain these groups in a ratio of monoisocyanurate groups to mono-allophanate groups of about 10:1 to 1:10, in some cases about 5:1 to 1:7.

Non-limiting examples of iminooxadiazine dione and optionally isocyanurate group-containing polyisocyanates include those that can be prepared in the presence of special fluorine-containing catalysts as described in U.S. Pat. No. 5,914,383, the pertinent portions of which are herein incorporated by reference. These polyisocyanates generally have an average NCO functionality of 3 to 3.5 and an NCO content of 5 to 30%, in some cases 10 to 25% and in other cases 15 to 25% by weight.

In an embodiment of the invention, the adhesive, sealant or coating compositions can include iii) an amine chain extender. According to particular aspects of this embodiment, the amine chain extender can include a $C_1$-$C_{24}$ linear, branched or cyclic alkyl, aryl, alkaryl, or aralkyl difunctional amine, optionally containing one or more —O—, —NH—, or —S— hetero atoms.

In an embodiment of the invention, the adhesive, sealant or coating compositions can be a two-component composition, where a first component comprises i) and a second component comprises ii). In a particular aspect of this embodiment, the first component further comprises iii) an amine chain extender.

In an embodiment of the invention, the adhesive, sealant or coating compositions can include one or more materials selected from leveling agents, wetting agents, flow control agents, antiskinning agents, antifoaming agents, fillers, adhesion promoters, viscosity regulators, plasticizers, pigments, dyes, UV absorbers, thermal stabilizers, antioxidants, and mixtures thereof.

Non-limiting examples of plasticizers that can be used in the present invention include dioctyl phthalate (DOP) dibutyl phthalate (DBP); diisodecyl phthalate (DIDP); dioctyl adipate isodecyl malonate; diethylene glycol dibenzoate, pentaerythritol ester; butyl oleate, methyl acetylricinoleate; tricresyl phosphate and trioctyl phosphate; polypropylene glycol adipate and polybutylene glycol adipate; and the like. Such plasticizers can be used alone or in combination of two or more.

Non-limiting examples adhesion promoters that can be used in the present invention include epoxy resins, phenolic resins, silane and amino silane coupling agents known in the art, alkyl titanates and/or aromatic polyisocyanates.

Non-limiting examples of cure catalysts, which may be used for curing, that can be used in the present invention include titanate esters, e.g., those of tetrabutyl titanate and tetrapropyl titanate; organotin compounds, e.g., dibutyl tin dilaurate, dibutyl tin maleate, dibutyl tin diacetate, tin octylate and tin naphthenate; lead octylate; amine-based compounds and salts of these compounds and carboxylates, e.g., butylamine, octylamine, dibutylamine, monoethanolamine, diethanolamine, triethanolamine, diethylenetriamine, triethylenetetramine, oleylamine, octylamine, cyclohexylamine, benzylamine, diethylaminopropylamine, xylylenediamine, triethylenediamine, guanidine, diphenylguanidine, 2,4,6-tris (dimethylamin-omethyl) phenol, morpholine, N-methyl morpholine, and 1,3-diazabicyclo(5,4,6) undecene-7 (DBU); low-molecular-weight polyamide resins produced by the reactions between excessive quantities of polyamines and polybasic acids; products of the reactions between excessive quantities of polyamines and epoxy compounds; and known silanol condensing catalysts, e.g., silane coupling agents containing amino group (e.g., $\gamma$-aminopropyl trimethoxy silane and N-($\beta$-aminoethyl)aminopropyl methyldimethoxy silane). These compounds may be used either individually or in combination.

Non-limiting examples of leveling agents that can be used in the present invention include cellulose, e.g., nitrocellulose and cellulose acetate butyrate.

Non-limiting examples of wetting agents that can be used in the present invention include glycols, silanes, anionic surfactants, and any other wetting agents known in the art.

Non-limiting examples of flow control agents, that can be used in the present invention include polyacrylic esters, non-ionic fluorinated alkyl ester surfactants, non-ionic alkylarylpolyether alcohols, silicones, and the like, as well as those available under the trade name RESIFLOW® by Estron Chemical, Inc., Parsippany, N.J., those sold under the trade name Benzoin® by DSM, Inc.; those available under the trade name MODAFLOW® from Monsanto and those available under the trade name SURFYNOL® available from Air Products, Bethlehem, Pa.

Non-limiting examples of antiskinning agents that can be used in the present invention include lecithin, oximes, non-limiting examples being butyraldehyde oxime and methyl ethyl ketoxime, hydroquinones, non-limiting examples being 2,5-di-t-butyl-hydroquinone and the methyl esters of hydroquinone and anthraquinones.

Non-limiting examples of antifoaming agents that can be used in the present invention include those available as FOAMEX® from Rohm and Haas Company, Philadelphia, Pa., those available under the trade name BYK®, available from BYK-Chemie USA, Wallingford, Conn., and those available under the trade name FoamBrake® from BASF Corp., Mount Olive, N.J.

Non-limiting examples of fillers that can be used in the present invention include fumed silica, settling silica, silicic anhydride, silicic hydrate, talc, carbon black, limestone powder, coated and uncoated colloidal calcium carbonate, coated and uncoated ground calcium carbonate, coated and uncoated precipitated calcium carbonate, kaolin, diatomaceous earth, fired clay, clay, titanium dioxide, bentonite, organic bentonite, ferric oxide, zinc oxide, activated zinc white, and fibrous fillers such as glass fibers or filaments. The filler can have any suitable particle size, in an embodiment of the invention, the filler particle size can be from 5 nm to 10 μm, in some cases 10 nm to 5 μm, and in other cases from 25 nm to 1 μm.

Non-limiting examples of viscosity regulators that can be used in the present invention include alkali-soluble, acid-soluble, and hydrophobically-modified alkali-soluble or acid-soluble emulsion polymers, those available as ACRYSOL® from Rohm and Haas Company, cellulosics, modified cellulosics, natural gums, such as xanthan gum, and the like.

Non-limiting examples of pigments that can be used in the present invention include silica, calcium carbonate, magnesium carbonate, titanium oxide, iron oxide and carbon black.

Non-limiting examples of dyes that can be used in the present invention include mordant dyes, i.e., dyes prepared from plants, insects, and algae, and direct dyes, non-limiting examples being those based on benzidine or benzidine derivatives.

Non-limiting examples of ultra violet light absorbers that can be used in the present invention include benzotriazole-based ultra violet ray absorbers, salicylate-based ultraviolet ray absorbers, benzophenone-based ultraviolet ray absorbers, hindered amine-based light stabilizers and nickel-based light stabilizers.

Non-limiting examples of thermal stabilizers that can be used in the present invention include HCl scavengers, a non-limiting example being epoxidized soybean oil, esters of beta-thiodipropionic acid, non-limiting examples being lauryl, stearyl, myristyl or tridecyl esters, mercaptobenzimidazole, the zinc salt of 2-mercaptobenzimidazole, zinc dibutyldithiocarbamate, dioctadecyl disulfide, pentaerythritol tetrakis-(beta-dodecylmercapto)-propionate, and lead phosphate.

Non-limiting examples of antioxidants that can be used in the present invention include 2,6-di-t-butyl phenol, 2,4-di-t-butyl phenol, 2,6-di-t-butyl-4-methyl phenol, 2,5-di-t-butyl-hydroquinone, n-octadecyl-3-(3,5-di-t-butyl-4-hydroxyphenyl)propionate, pentaerythrityl-tetrakis[3-(3,5-di-t-butyl-4-hydroxyphenyl)propionate], 2,2'-methylenebis(4-methyl-6-t-butyl phenol), 4,4'-butylidenebis(3-methyl-6-t-butyl phenol), 4,4'-thiobis(3-methyl-6- -t-butyl phenol), N,N'-diphenyl-p-phenylenediamine, 6-ethoxy-2,2,4-trimethyl-1,2- -dihydroquinoline and the antioxidants available under the trade name IRGANOX® from Ciba Specialty Chemicals, Basel, Switzerland.

The present invention also provides a method of joining a first adherend or substrate and a second adherend or substrate. The method includes applying the above-described adhesive composition containing components i), ii), and optionally iii) to at least a portion of a surface of the first adherend and optionally to at least a portion of a surface of the second adherend;

contacting the adhesive composition containing surface of the first adherend with a surface of the second adherend, where at least one of the contacting surfaces has the composition applied thereto, to form a bonded assembly; and curing the adhesive compositions in the bonded assembly.

The method of joining provides an assembly. The assembly includes the first adherend and the second adherend, which independently include one or more materials selected from wood, metals, plastics, paper, ceramics, minerals, stone, glass, and concrete.

In a particular embodiment of the invention, the metal can include iron or aluminum. In another particular embodiment of the invention, the plastic can include poly(ethylene), poly (propylene), poly(ethylene terephthalate), and mixtures thereof.

In an embodiment of the invention, the first substrate and the second substrate are contacted at a temperature of from 0° C. to 150° C. Also the first substrate and the second substrate can be contacted at a pressure of from atmospheric pressure to 500 psi.

Embodiments of the present invention are also directed to assemblies made according to the above described method where at least the first adherend or substrate and the second adherend or substrate bonded together.

Other embodiments of the invention are directed to an adhesive, sealant or coating composition that includes:

i) the functional aspartate of claim 16, ii) an isocyanate functional material as described above, and optionally iii) an amine chain extender as described above.

Another embodiment of the present invention is directed to a method of coating a substrate that includes applying the above-described coating composition including components i), ii), and optionally iii), to at least a portion of a surface of the substrate. The invention also provides the coated substrate prepared according to the above-described method. As such, the substrate can be, but is not limited to one or more materials selected from wood, metals, plastic, paper, ceramics, minerals, stone, glass, and concrete. In particular embodiments, the substrates can include wood, metals such as ferrous substrates and aluminum substrates, and plastics.

The coating composition can be applied by conventional means including brushing, dipping, flow coating, spraying, and the like. Upon application to a substrate, the composition is allowed to coalesce to form a substantially continuous film on the substrate. The film is formed on the surface of the substrate by driving off liquids out of the film by heating or by an air drying period.

Further embodiments of the invention are directed to coating compositions that are two-component compositions, where a first component includes i) and optionally iii), and a second component includes ii).

An embodiment of the present invention is directed to a method of applying a composition to a substrate that includes mixing component i) and component ii), as described above, together.

The present invention is more particularly described in the following examples, which are intended to be illustrative only, since numerous modifications and variations therein will be apparent to those skilled in the art. Unless otherwise specified, all parts and percentages are by weight.

Example 1

This example demonstrates the synthesis of diethyl 2-(2-methyl-1-aziridinyl) succinate, an intermediate according to the present invention. Using a round-bottom flask equipped with a thermocouple, stirrer, nitrogen inlet, addition funnel and cold finger, 8.08 g (0.1415 mol) of 2-methyl aziridine was combined with diethyl maleate (24.36 g, 0.1415 mol) keeping the temperature below 30° C. and stirring overnight. A vacuum was applied to remove unreacted 2-methyl aziridine. Gas Chromatography (GC) was used to verify completion of the reaction.

Examples 2-9

Aspartate-Functional compounds were prepared by combining the product from Example 1 with an active hydrogen containing compound at room temperature in a round bottom flask equipped with a stirrer at a 1:1 equivalent ratio of the product from Example 1: active hydrogen compound. GPC and GC were used to confirm completion of the reaction. Specific examples are listed in the following table.

The Aspartate-Functional compounds were hand mixed with a polyisocyanate (DESMODUR® N-3300) at a NCO:NH ratio of 1:1. The Shore A hardness and Shore D hardness were determined in accordance with DIN 53505 and ASTM D2240. Tensile strength and elongation at break were determined on an INSTRON® 4444, Instron Corp., Canton, Mass., in accordance with DIN/ISO 527.

The table below shows specific results.

| Example No. | Active Hydrogen Compound | Shore A | Shore B | Tensile Strength | Elongation (%) |
|---|---|---|---|---|---|
| 2 | Polyester A[1] | 56 | 8 | 149 | 144 |
| 3 | Polyester B[2] | 66 | 13 | 587 | 112 |
| 4 | Adipic Acid | — | 55 | 1351 | 144 |
| 5 | Adipic Acid | — | 63 | 2247 | 140 |
| 6 | Polyether A[3] | 32 | — | 419 | 224 |
| 7 | Polyether B[4] | 76 | — | 2552 | 80 |
| 8 | Polyether C[5] | 54 | — | 924 | 111 |
| 9 | Polyether D[6] | 80 | — | 2240 | 45 |

[1]Polyester of adipic acid, 1,6-hexanediol, and neopentylglycol with a number average molecular weight (Mn) of 1030.
[2]Polyester of adipic acid, 1,6-hexanediol, neopentylglycol, trimethylolpropane with a Mn of 1275.
[3]Acid functional polyether prepared by reacting a polyether with hydroxyl functionality of 2 and Mn of 425 MULTRANOL ® 9121 available from Bayer, reacted with hexahydrophthalic anhydride, as described in U.S. Pat. No. 6,384,175.
[4]Acid functional polyether prepared by reacting a polyether with hydroxyl functionality of 5.8 and Mn of 859, MULTRANOL ® 4030 available from Bayer, with hexahydrophthalic anhydride as described in U.S. Pat. No. 6,384,175.
[5]Acid functional polyether prepared by reacting a polyether with hydroxyl functionality of 3 and Mn of 439, MULTRANOL ® 4035 available from Bayer, with hexahydrophthalic anhydride, as described in U.S. Pat. No. 6,384,175.
[6]Acid functional polyether prepared by reacting a polyether with hydroxyl functionality of 5 and Mn of 625, MULTRANOL ® 4034 available from Bayer, with hexahydrophthalic anhydride, as described in U.S. Pat. No. 6,384,175.

Examples 10-12

Aspartate-Functional compounds were prepared by combining the product from Example 1 with a combination of two active hydrogen containing compounds as described above. The Aspartate-Functional compounds were then hand mixed with DESMODUR® N-3300 at a NCO:NH ratio of 1:1 as described above. Evaluations were made as described above, the results of which are shown in the table below.

| Example No. | Active Hydrogen Compound | | Shore A | Tensile Strength | Elongation (%) |
|---|---|---|---|---|---|
| | No. 1 | No. 2 | | | |
| 10 | Polyester C[7] | Amine functional resin[8] | 48 | 665 | 126 |
| 11 | Polyester C[7] | Polyamine[9] | 59 | 1073 | 97 |
| 12 | Polyester C[7] | Urethane bisazodine | 40 | 432 | 78 |

[7]acid terminated polyester made from adipic acid, hexanediol, neopentyl glycol and trimethylol propane.
[8]DESMOPHEN ® NH1420 available from Bayer Corporation, Pittsburgh, PA.
[9]Imine functional polyamine Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An adhesive, sealant or coating composition comprising:
i) the functional dialkyl aspartate according to the formula

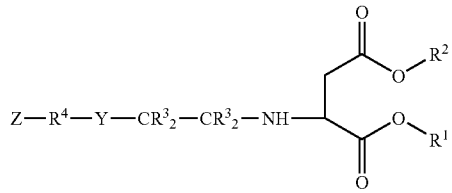

wherein
$R^1$ and $R^2$ are independently $C_1$-$C_8$ linear, branched or cyclic alkyl,
each occurrence of $R^3$ is independently selected from H, $C_1$-$C_{20}$ linear, branched, or cyclic alkyl, aryl, alkaryl or aralkyl,
Y is a linking group selected from the group consisting of
—O—, —S—, —NR$^5$—,
—O—P(O)$_2$—O—, —P(O)$_2$—O—, —S(O)$_2$—O—,

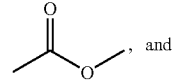, and a group resulting from the removal of an acidic hydrogen from a carbon that is positioned adjacent to one or more electron withdrawing groups according to one of the formulas

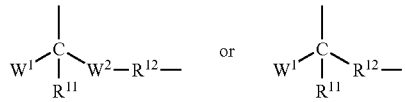

wherein

R$^5$ is H or C$_1$-C$_3$ linear or branched alkyl,

W$^1$ is an electron withdrawing group selected from the group consisting of nitrile, R$^{11}$—CO—, nitro, carboxylic acids and their corresponding salts, C$_1$-C$_{24}$ linear, branched or cyclic alkyl, alkenyl, aryl, alkaryl, or aralkyl esters of carboxylic acids, and C$_1$-C$_{24}$ linear, branched or cyclic alkyl sulfonyl, W$^2$ is a ketone, R$^{11}$ is selected from H, —OH, C$_1$-C$_{24}$, linear, branched or cyclic alkyl, aryl, alkaryl, or aralkyl, which may contain one or more hetero atoms selected from O, S, and/or N, R$^{12}$ is C$_1$-C$_{24}$ linear, branched or cyclic alkylene arylene, alkarylene, or aralkylene, which may contain one or more hetero atoms selected from O, S, and/or N, and R$^4$ is a linking group selected from the group consisting of C$_1$-C$_{24}$ linear, branched or cyclic alkylene, arylene, alkarylene, or aralkylene, —(—[CHR$^7$—]$_n$—(O—)p—R$^8$—, wherein R$^7$ is C$_1$-C$_3$ linear or branched alkyl or alkylol, n is 1 to 4, and p is 1 to 1,000,

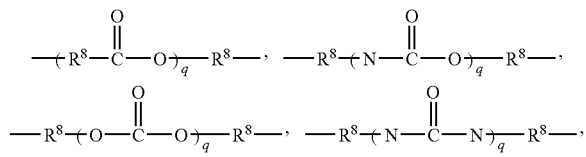

wherein q is 1 to 1,000, and each occurrence of R$^8$ is independently selected from C$_1$-C$_{24}$ linear, branched or cyclic alkylene, alkenylene, arylene, alkarylene, or aralkylene, optionally including substituent hydroxyl, carboxylic acid, or C$_1$-C$_8$ linear, branched or cyclic carboxylic acid ester groups,

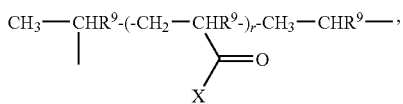

wherein r is 1 to 10,000,

R$^9$ is C$_1$-C$_3$ linear or branched alkyl,

X is —OR$^{10}$ or —NR$^5{}_2$, where R$^5$ is as defined above,

R$^{10}$ is H or C$_1$-C$_{24}$ linear, branched or cyclic alkyl, aryl, alkaryl, and aralkyl, and combinations thereof, and Z is selected from the group consisting of —H, —OR$^{10}$, —R$^4$—OR$^{10}$, —NR$^5{}_2$, —R$^4$—NR$^5{}_2$, —SH, —R$^4$—SH,

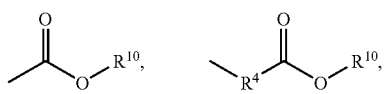

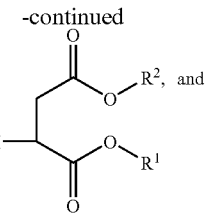

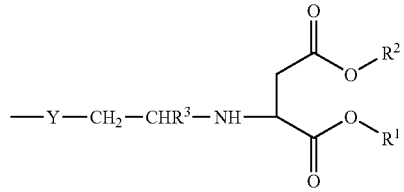

ii) an isocyanate functional material.

2. The composition of claim 1, wherein the isocyanate functional material is a polyisocyanate containing from 2 to 6 isocyanate groups.

3. The composition of claim 2, wherein the polyisocyanate has a structure according to the formula:

OCN—R$^{17}$—NCO wherein R$^{17}$ is selected from C$_2$ to C$_{24}$ linear, branched, and cyclic alkylene, arylene, and aralkylene, which may optionally contain one or more isocyanate groups.

4. The composition of claim 2, wherein the polyisocyanate is selected from the group consisting of 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane, bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α,α',α'-tetramethyl-1,3-diisocyanate, α,α,α',α'-1,4-xylylene diisocyanate, 1-isocyanato-1-methyl-4(3)-isocyanatomethyl cyclohexane, 2,4-hexahydrotoluylene diisocyanate, 2,6-hexahydrotoluylene diisocyanate, 1,3-phenylene diisocyanate, 1,4-phenylene diisocyanate, 2,4-toluylene diisocyanate, 2,6-toluylene diisocyanate, 2,4-diphenyl-methane diisocyanate, 4,4'-diphenyl-methane diisocyanate, 1,5-diisocyanato naphthalene and mixtures thereof.

5. The composition of claim 1, further comprising one or more materials selected from the group consisting of leveling agents, wetting agents, flow control agents, antiskinning agents, antifoaming agents, fillers, adhesion promoters, viscosity regulators, plasticizers, pigments, dyes, UV absorbers, thermal stabilizers, antioxidants, and mixtures thereof.

6. The composition according to claim 1 comprising iii) an amine chain extender.

7. The composition according to claim 6, wherein the amine is a C$_1$-C$_{24}$ linear, branched or cyclic alkyl, aryl, alkaryl, or aralkyl difunctional amine, optionally containing one or more —O—, —NH—, or —S— hetero atoms.

8. The composition of claim 1 as a two-component composition, wherein a first component comprises i) and a second component comprises ii).

9. The composition according to claim 8, wherein the first component further comprises iii) an amine chain extender.

10. A method of applying a composition to a substrate comprising mixing component i) and component ii) of claim 8.

11. A method of bonding a first substrate to a second substrate comprising applying a coating of the composition of claim 1 to at least one surface of the first substrate or the second substrate, and contacting a surface of the first substrate with a surface of the second substrate, wherein at least on of the contacting surfaces has the coating applied thereto.

12. The method of claim 11, wherein one or both of the first substrate and the second substrate comprises a substrate selected from the group consisting of wood, metals, plastics, paper, canvas, ceramics, stone, glass, and concrete.

13. The method of claim 12, wherein the metal comprises iron or aluminum.

14. The method of claim 12, wherein the plastic is selected from the group consisting of poly(ethylene), poly(propylene), poly(ethylene terephthalate), and mixtures thereof.

15. The method of claim 11, wherein the first substrate and the second substrate are contacted at a temperature of from 0° C. to 150° C.

16. The method of claim 11, wherein the first substrate and the second substrate are contacted at a pressure of from atmospheric pressure to 500 psi.

17. An assembly made according to claim 11 comprising at least the first substrate and the second substrate bonded together.

18. A method of coating a substrate comprising applying the composition of claim 1 to at least a portion of a surface of the substrate.

19. A coated substrate prepared according to the method of claim 18.

* * * * *